(12) United States Patent
Kulin et al.

(10) Patent No.: US 11,588,814 B2
(45) Date of Patent: *Feb. 21, 2023

(54) BIOMETRIC PATIENT IDENTITY VERIFICATION SYSTEM

(71) Applicant: PulseONE Global, LLC, Savannah, GA (US)

(72) Inventors: Sandor Kulin, Budapest (HU); Balazs Szabo, Budapest (HU); Daniel Kulin, Budapest (HU)

(73) Assignee: PulseONE Global, LLC, Savannah, GA (US)

(*) Notice: Subject to any disclaimer, the term of this patent is extended or adjusted under 35 U.S.C. 154(b) by 202 days.

This patent is subject to a terminal disclaimer.

(21) Appl. No.: 17/169,902

(22) Filed: Feb. 8, 2021

(65) Prior Publication Data

US 2021/0168137 A1    Jun. 3, 2021

Related U.S. Application Data

(63) Continuation of application No. 16/170,435, filed on Oct. 25, 2018, now Pat. No. 10,958,643.

(51) Int. Cl.
| | |
|---|---|
| *H04L 9/40* | (2022.01) |
| *G16H 40/67* | (2018.01) |
| *A61B 5/00* | (2006.01) |
| *A61B 5/1172* | (2016.01) |
| *A61B 3/117* | (2006.01) |
| *A61B 5/318* | (2021.01) |

(52) U.S. Cl.
CPC .......... *H04L 63/0861* (2013.01); *A61B 3/117* (2013.01); *A61B 5/0022* (2013.01); *A61B 5/1172* (2013.01); *A61B 5/318* (2021.01); *A61B 5/489* (2013.01); *G16H 40/67* (2018.01)

(58) Field of Classification Search
CPC .. H04L 63/0861; H04L 9/3231; H04W 12/06; H04W 4/38; A61M 2205/609; A61B 5/1172

See application file for complete search history.

(56) References Cited

U.S. PATENT DOCUMENTS 9,305,155 B1 *   4/2016   Vo ...................... G06F 3/04817
10,958,643 B2    3/2021   Kulin (Continued)

OTHER PUBLICATIONS

Kulin, MD, Sandor; Final Office Action for U.S. Appl. No. 16/170,435, filed Oct. 25, 2018, dated Jul. 7, 2020, 17 pgs.

(Continued)

*Primary Examiner* — Ali S Abyaneh
(74) *Attorney, Agent, or Firm* — Taylor English Duma LLP

(57) ABSTRACT

A system for determining identification of a patient communicating over a computer network with a medical provider with certainty is provided using biometric data captured by said medical provider with subsequent biometric data generated by biometric sensors proximal to a patient. Using previously captured biometric information concerning physical characteristics unique to the patient and comparing such to subsequently generated biometric data from the patient, a medical provider can determine the identity of a patient attempting communication over a computer network with the medical provider.

15 Claims, 1 Drawing Sheet

(56) References Cited

U.S. PATENT DOCUMENTS

| | | | |
|---|---|---|---|
| 2002/0099572 A1* | 7/2002 | Dyckman | G16H 15/00 |
| | | | 705/3 |
| 2006/0110011 A1* | 5/2006 | Cohen | H04L 63/0861 |
| | | | 382/115 |
| 2007/0258626 A1* | 11/2007 | Reiner | G16H 40/20 |
| | | | 340/5.82 |
| 2011/0288874 A1 | 11/2011 | Hinkamp | |
| 2014/0325577 A1* | 10/2014 | Garcia Mendoza | H04N 21/231 |
| | | | 725/115 |
| 2017/0142087 A1* | 5/2017 | Maninder | H04L 9/3297 |
| 2020/0137051 A1 | 4/2020 | Kulin et al. | |

OTHER PUBLICATIONS

Kulin, Sandor; Non-Final Office Action for U.S. Appl. No. 16/170,435, filed Oct. 25, 2018, dated Feb. 19, 2020, 11 pgs.
Kulin, Sandor; Notice of Allowance for U.S. Appl. No. 16/170,435, filed Oct. 25, 2018, dated Nov. 13, 2020, 19 pgs.
Sandor, Kulin; Advisory Action for U.S. Appl. No. 16/170,435, filed Oct. 25, 2018, dated Aug. 28, 2020, 3 pgs.

* cited by examiner

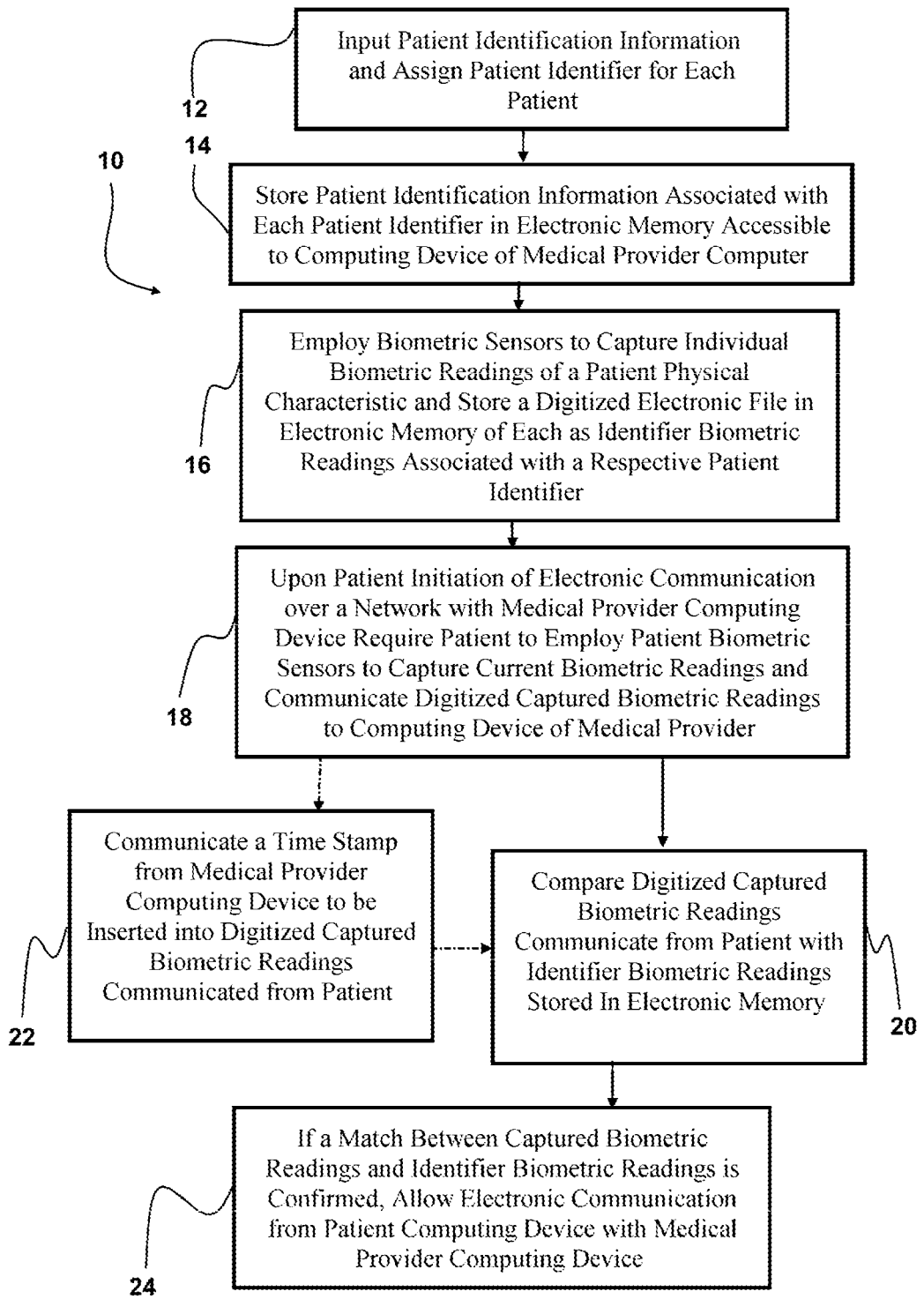

BIOMETRIC PATIENT IDENTITY VERIFICATION SYSTEM

CROSS-REFERENCE TO RELATED APPLICATIONS

The present application is a continuation U.S. application Ser. No. 16/170,435 filed Oct. 25, 2018 which is hereby incorporated by reference herein in its entirety.

FIELD OF THE INVENTION

The present device relates to patient identification during remote health monitoring. More particularly, the method and apparatus herein relates to a system for capturing a biometric identifier of a patient which is communicated to a remote health provider and verified prior to subsequent communication of health information of that patient.

BACKGROUND OF THE INVENTION

With the evolution of personal computing devices and smartphones and pad computers and the like in recent years, advances have been achieved in the ability for patients to ascertain health conditions as well as problems remotely. Through the employment of biometric sensors and monitoring devices which are in wired or wireless communication with a computing device running software adapted to the task of converting received sensor data to conventional test outputs, patients can monitor or test themselves for a wide variety of health issues.

Such computing devices in recent years have evolved to be able to communicate data over wireless and wired networks, to virtually any point on the globe. As a consequence, physicians and medical providers have been provided with a valuable means to actually monitor patients and their health conditions in real time rather than just examining such patients on rare or even scheduled visits to the health provider. As can be discerned, the ability to test and monitor patients for known or suspected health conditions remotely and frequently, provides an exceptionally valuable tool to physicians and health providers in the monitoring of known health conditions as well as in testing over time durations for diagnosing unknown but suspected health conditions.

For example, a heart patient having suspected heart rhythm disturbance called bradycardia, where the heartbeat slows, may actually present in an office visit after the exercise provided by walking through parking lots and hallways, as having a normal heartbeat. However, upon arriving home and relaxing, the condition may return and if not diagnosed and treated promptly, can cause severe problems such as hypoxia and even life threatening issues. There are many such conditions which are not conclusively ascertainable by the physician during a visit by the patient to the medical facility. The ability of the patient thus, to remotely test for a suspected condition over time and provide results to the physician of such testing, is consequently a valuable tool in the early and accurate diagnosis of a health problem which appears inconsistently.

However, issues exist concerning the provision of such testing data from the patient in remote locations. First and foremost for the physician is the proper identification of the patient identity before employing the transmitted testing data from a remote source. Should the data from the wrong patient be communicated and employed for a different patient, the physician can make a diagnosis resulting in great harm to the patient to which the wrong data is applied. Further, in some cases, patients have been known to fraudulently submit testing data from other persons as their own. As such, it is critical that the physician or medical service provider, receiving a data stream correlating to a health condition test, be certain, without any doubt, that the data received relates only to a single patient.

The system herein provides a method for positively identifying data or a data stream communicated to a remote medical provider, as being specifically related to a single Person or patient. Using one or preferably a plurality of biometric readings from a patient, which when electronically communicated to the medical provider, the identity of the patient may be confirmed with certainty by comparing the transmitted biometric readings to stored such readings which are pre authenticated as matching a single patient. It thus provides medical providers a means to ascertain, with certainty, that the medical testing data being communicated over a network to that medical provider, is associated and concerns only one possible patient. Further, the system prevents fraudulent medical testing or monitoring information from being transmitted to the medical provider over the network either intentionally by the patient or unintentionally by third parties.

The forgoing background and examples of patient authentication through the employment of biometric readings are intended to be illustrative and not exclusive, and they do not imply any limitations on the invention described and claimed herein. Various other limitations of the related art are known or will become apparent to those skilled in the art upon a reading and understanding of the specification below and the accompanying drawings.

SUMMARY OF THE INVENTION

The system herein employs biometric sensing components providing data concerning the health of a patient which can be transmitted over a computer network. Using sensed biometric information about a patient sending electronic information to a medical provider over a network, medical providers and physicians can identify the patient with certainty and employ the communicated testing information only for the correctly identified patient. In this manner medical providers can employ the communicated information only to the correctly identified patient and also be assured that the data communicated is not fraudulent or gathered from another individual. It thus provides medical providers with certainty as to the identification of the patient and that the data being communicated is only from that patient.

In the system, each patient is subjected to standardized biometric testing for one or preferably a plurality of medical biometric readings of a patient that can only be associated with that individual patient. For example the electrocardiogram (EKG) of individual when traced on paper or a display, is a reliable identifier of each individual patient. This is because each heart beats uniquely and generates an EKG trace which can be associated with the individual patient. Thus, an EKG of a patient taken during an office visit can be stored in electronic memory associated with that individual patient and act as an electronic identifier of that individual patient at a later date by comparing the stored EKG to one taken in real time remotely.

Another biometric identifier is a fingerprint, which can be digitized to an electronic fingerprint file and stored in electronic memory in association with an individual patient. Subsequently, an electronic fingerprint inputs from a fingerprint sensor remotely from the patient, can be matched to the stored electronic fingerprint to ascertain a match and the identity of the patient.

Another biometric identifier unique to a patient is an iris scan. In the system an iris scan of the patient is digitized and stored in the electronic memory of a database as matching an individual patient. Subsequently, a remote image capturing device such as an electronic camera or cell phone camera can capture the iris image of a patient, and communicated over a network to a medical provider. The received digitized image communicated by the patient can then be compared with the digitized image stored in electronic memory associated with a patient to ascertain a match to confirm the identity of the patient sending the image.

Another biometric identifier employable in the system herein, is a digital image of capillaries of an individual finger of a patient captured using a pulse oximeter device with an image capturing and transmitting component. Every patient has a unique pattern to the capillaries in each finger upon which a pulse oximeter is engaged to ascertain heart rate and oxygen saturation of the bloodstream. In the system herein, during a visit to the medical provider, a biometric reading of an image of the capillaries of one or a plurality of fingers is captured and digitized and associated with the individual patient. Subsequently, the patient will employ a biometric sensor engaged to a networked computing device, such as a capillary image capturing pulse oximeter, to capture a digital image of the capillary pattern of a chosen finger. That digitized capillary image is then transmitted to the medical provider and compared with the digitized capillary image or images associated with the purported individual patient. A match will authenticate the patient sending the digitized capillary image over a network such as the internet, as the known patient.

As such, in the system herein, one, or more preferably a plurality of digitized biometric readings of a patient are taken using biometric sensors remotely, digitized, and then communicated to a medical provider as a means to first identify the patient with certainty. Only thereafter will testing telemetry or digitized information concerning medical monitoring or testing, communicated remotely over a network from the computing device of the patient, be associated to the patient identified using the digitized matching, and thereby used for diagnosis by the medical provider.

An additional layer of security may be provided in a manner to prevent patients or imposters of patients, from storing digitized iris images, capillary images, or fingerprints, and then communicating such to the medical provider to authenticate a user. In this mode of the system, software running on the computing device of the medical provider, can transmit a time stamp to be included in metadata of each digitized file sent by the patient during authentication. In this fashion, only a real time capturing of biometric attributes of the patient will be enabled to insert the time stamp in meta data or digitized imaging of the biometric attribute of the patient being requested by the medical provider and subsequently sent by the networked computing device of the patient. Additionally, software running on the medical provider computing device in communication over the network with the patient computing device may designate a plurality of biometric readings of individual patient physical or biological characteristics to be sent by the patient device using local biometric sensors, in a particular order of the plurality requested.

With respect to the above description, before explaining at least one preferred embodiment of the herein disclosed patient identity authentication system invention in detail, it is to be understood that the invention is not limited in its application to the details of construction and to the arrangement of the steps or use of components in the following description or illustrated in the drawings. The patient authenticating system invention herein described and shown is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other biometric sensing patient authentication systems for carrying out the several purposes of the present disclosed system herein. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. By "computer or computing device" is meant any computing device having electronic memory and operating software to the task noted. By "networked" or "connected by a network" is meant any computer network enabling electronic communication between two computing devices, for example and in no way limiting, a cellular communication system and/or the Internet. The term "substantially" when employed herein, means plus or minus twenty percent unless otherwise designated in range.

It is an object of the present invention to provide a system for patient identity verification during communications over a network, which employs one or preferably a plurality of digitized real time captured biometric readings from a patient.

It is an additional object of this invention to provide such an identity verification system which allows the medical provider to designate the biometric data to be communicated within a designated time duration and/or to require a response with a communicated time stamp before lapse of a time duration.

These and other objects, features, and advantages of the biometric patient identification system, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF DRAWING FIGURES

The accompanying drawings, which are incorporated herein and form a part of the specification, illustrate some, but not the only or exclusive examples of embodiments and/or features of the disclosed biometric patient identity verification system. It is intended that the embodiments and FIGURE disclosed herein are to be considered illustrative of the invention herein, rather than limiting in any fashion.

In the drawings:

FIG. 1 depicts a flow chart of method and apparatus for biometric patient identity verification for communications over a network between a medical provider and patient.

DETAILED DESCRIPTION OF THE INVENTION

In this description, the directional prepositions of up, upwardly, down, downwardly, front, back, top, upper, bottom, lower, left, right and other such terms refer to the device as it is oriented and appears in the drawings and are used for convenience only and such are not intended to be limiting or to imply that the device has to be used or positioned in any particular orientation.

Now referring to the flow chart in FIG. 1, there is seen a generalized flow chart of the system 10 herein for determining patient identification prior to communications from patients with medical providers over a network. Such communications for example can occur where patients are remotely monitoring a medical condition or monitoring a body function over time and communicating captured information in electronic form to a medical provider. For example a patient with inconsistent symptoms of a heart problem, which are not easily determined in a simple office visit, can be provided with monitoring equipment or software adapted to monitor a medical condition using a smartphone or computer, and communicate testing results electronically over a time duration.

Also by example, but in no way limiting, is monitoring for sleep apnea. Such is not easily done in sleep centers because patients are kept awake by unfamiliar surroundings and noise so an electronic home monitoring device is preferably employed to monitor sleep at home over a duration of evenings. In such cases the patient could use the testing equipment to capture sleep apnea readings which may be communicated to the health provider over a network connection from the device itself or a user computing device. Of course, any condition that may be tested or remotely monitored electronically and reported electronically to the medical provider is anticipated within the scope of this system, so long as the patient identity sending the electronic information can first be determined without doubt, using digitized biometric information concerning the patient captured remotely.

In a first step in the system 12 during a visit to the medical provider such as a doctor or medical facility, patient identification information would be obtained, including but not limited to legal identification, address, contact information, insurance information, and other relevant patient identification information. The patient would generally be assigned or associated with a patient identifier which may be alphanumeric or otherwise.

In a next step in the system 14 this patient identification information in an association with the patient identifier, is stored in electronic memory accessible to the computing device of the medical provider. This patient identifier and patient identification information is employed and added to so long as the patient is served by the medical provider.

In a following or third step 16, at the facility of the medical provider or an affiliated facility, biometric sensors are employed to capture biometric readings of one or a plurality of patient physical or body or health or functional characteristics. Such biometric sensors may include one or a combination of a digital fingerprint capturing device, a pulse oximeter, an imaging device to capture the capillary pattern formed by capillaries in a finger of the patient, an imaging device to capture the iris of the eye, and an electrocardiograph machine. The electronic signal of the image or electrical performance of the body part captured by the biometric sensor, is communicated to a computing device and digitized into a digital identifier of the respective body part imaged or captured or tracked electronically.

In the case of a biometric sensor, in the form of a digital fingerprint capturing device, it will generate a digital image of a fingerprint which may later be compared. A biometric sensor provided by a pulse oximeter may be combined with an imaging device which will employ the light transmitted through a finger, to capture a digital image of a capillary pattern formed by capillaries in a finger, which may later be compared to another such capillary pattern image. In the case of a biometric sensor for imaging the iris of the eye, a digital image is generated which may later be employed for comparison to a subsequent iris digital image.

In the case of a biometric senor, which generates an EKG, the electrical impulse (or "wave") travels through the heart will conventionally show a line graph depicting the timing of the top and lower chambers where a P-wave is generated by the upper chambers and a QRS complex is generated by the right and left bottom chambers, followed by a T-wave generated during recovery or return to a resting state for the ventricles. This resulting EKG can be like an electronic heart fingerprint and highly identifiable to individual patients. When digitized, the EKG can later be employed in comparison to a transmitted EKG taken remotely in identifying the patient.

As noted, in this third step 16, each biometric sensor will generate a respective biometric reading of a particular physical characteristic of the patient, which is digitized and stored in electronic memory as associated with a single patient.

In a following or fourth step 18, when a patient having an identifier and biometric readings associated with that patient, initiates electronic communication from a patient computing device or a testing device in their possession, over an electronic network such as the internet, the computing device of the medical provider will first seek validation of the patients identification. To that end, prior to allowing communication of test or monitoring data from the patient, software running on the computing device of the medical provider, will require the patient to employ patient biometric sensors in the location of the patient, and to capture current biometric readings of one or a plurality of patient physical characteristics or functions and to communicate digitized output of the biometric sensors, over the network to the medical provider computing device.

The same biometric sensors employed by the medical provider in the third step 16 are employed at this remote location of the patient at this subsequent time. Preferably, the patient is required to communicate digitized readings from at least two of the biometric sensors such as any two from the group including a digital fingerprint capturing device, an imaging device to capture the capillary pattern formed by capillaries in a finger of the patient, an imaging device to capture the iris of the eye, or a digitized EKG from a one or more lead electrocardiograph which are currently available for engagement to computers and cell phones.

Upon receipt of the digitized current captured biometric readings of from the patient biometric sensors, in a comparison step 20, such are compared with the digitized identifier biometric readings captured by the medical provider in step 16 and stored in as identifier biometric readings in electronic memory.

In a step subsequent 20, if a match between captured biometric readings and the identifier biometric readings is determined, the identification of the patient is determined as a match and electronic communications from the patient computing device or a testing device in their possession, will be accepted by the medical provider computing device and stored in electronic memory in association with the patient identifier for use by physicians and staff.

At optional step 22, a marker or time-stamp requirement may also be implemented after step 18 but before step 20, in order to prevent a party from storing pre-captured biometric readings using biometric sensors on the patient, and storing them to send when requested in step 18. In this step 22, a digital time stamp, is communicated from the medical provider computing device which is required to be included in meta data or as part of the digitized files sent by the patient in response to step 18 for such biometric digital information. In this step, should the time stamp not be included in the digitized biometric readings, a match 24 will not be ascertained and communication denied. Also in this step, the response from the patient may be required to occur within a time duration such as 2-5 minutes to give them time to generate biometric readings but not substitute files.

While the present system has been described herein with reference to particular embodiments thereof and/or steps in the method of production or use, a latitude of modifications, various changes and substitutions are intended in the foregoing disclosure, and it will be appreciated that in some instance some features, or configurations, of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of any abstract included with this specification is to enable the U.S. Patent and Trademark Office, the public generally, and especially the scientists, engineers, and practitioners in the art who are not familiar with patent or legal terms or phraseology, to determine quickly from a cursory inspection the nature and essence of the technical disclosure of the application. Any such abstract is neither intended to define the invention of the application, which is measured by the claims, nor is it intended to be limiting, as to the scope of the invention in any way.

What is claimed is:

1. A method for verifying an identity of a patient communicating over a computer network with a medical provider, comprising:
    employing a provider biometric sensor to capture a biometric reading of an individual physical characteristic of a patient;
    storing the biometric reading as a captured digitized electronic file relating only to the patient;
    upon initiation of electronic communication from a patient computing device to a provider computing device over a network, communicating a time stamp from the provider computing device, requiring the patient to employ a patient biometric sensor to generate a current biometric reading for the individual physical characteristic of the patient, and to communicate to the provider computing device the current biometric reading and metadata, wherein the metadata incorporates the time stamp;
    comparing the current biometric reading with the captured digitized electronic file and the metadata to the time stamp to ascertain either a match or non-match therebetween; and
    permitting transmission of health information from the patient computing device to the provider computing device only upon ascertaining a match between the current biometric reading and the captured digitized electronic file and between the metadata and the time stamp.

2. The method for verifying the identity of a patient communicating over a computer network with a medical provider of claim 1, further comprising the step of requiring the patient to communicate the current biometric reading and the metadata to the provider computing device within a determined time duration subsequent to the communicating of the time stamp.

3. The method for verifying the identity of a patient communicating over a computer network with a medical provider of claim 1, wherein the biometric reading is selected from a group of biometric readings including a digital fingerprint, a digital image of a capillary pattern in a finger, a digital image of an iris, and a digitized electrocardiograph.

4. A system for verifying an identity of a patient, comprising:
    a provider biometric sensor for capturing biometric data associated with a patient; and
    a provider computer, wherein the provider computer is to:
        store the biometric data associated with the patient;
        provide, to a patient computer in response to a communication from the patient computer, a time stamp and a request for a digitized file containing patient biometric data;
        receive, from the patient computer, the digitized file containing patient biometric data and metadata, the metadata associated with the patient biometric data and including the time stamp;
        determine if the metadata includes the time stamp provided by the provider computer;
        determine if the patient biometric data matches the biometric data associated with the patient and stored by the provider computer; and
        receive current health-related information from the patient computer only if the metadata includes the time stamp provided by the provider computer and the patient biometric data matches the biometric data associated with the patient and stored by the provider computer.

5. The system for verifying the identity of a patient of claim 4, wherein the provider computer is further configured to:
    determine if the patient biometric data and metadata were received within a predetermined time duration after the time stamp is provided to the patient computer.

6. The system for verifying the identity of a patient of claim 4, wherein the provider biometric sensor comprises an electrocardiogram machine and the biometric data comprises an electrocardiogram.

7. The system for verifying the identity of a patient of claim 4, wherein the provider biometric sensor comprises an iris scanner and the biometric data comprises an iris scan.

8. The system for verifying the identity of a patient of claim 4, wherein the provider biometric sensor comprises a fingerprint sensor and the biometric data comprises a fingerprint.

9. The system for verifying the identity of a patient of claim 4, wherein the provider biometric sensor comprises a capillary image capturing pulse oximeter and the biometric data comprises an image of capillaries.

10. A system for verifying an identity of a patient, comprising:
   a patient biometric sensor for capturing biometric data associated with a patient; a sensor for collecting health-related data associated with the patient; and
   a patient computer associated with the patient, wherein the patient computer is configured to:
      store the health-related data collected with the sensor and associated with the patient;
      initiate communication with a provider computer in order to transmit the health-related data to the provider computer;
      receive, from the provider computer, a time stamp and a request for biometric data associated with the patient;
      capture the biometric data requested by the provider computer;
      create metadata associated with the biometric data, the metadata including the time stamp;
      transmit the biometric data and the metadata to the provider computer; and transmit the health-related data to the provider computer upon receipt of an approval by the provider computer, the approval being based on verification of the biometric data and the time stamp included in the metadata.

11. The system for verifying the identity of a patient of claim 10, wherein the patient computer is further configured to:
   provide the biometric data and metadata within a predetermined time duration after the time stamp is received from the provider computer.

12. The system for verifying the identity of a patient of claim 10, wherein the patient biometric sensor comprises an electrocardiogram machine and the biometric data comprises an electrocardiogram.

13. The system for verifying the identity of a patient of claim 10, wherein the patient biometric sensor comprises an iris scanner and the biometric data comprises an iris scan.

14. The system for verifying the identity of a patient of claim 10, wherein the patient biometric sensor comprises a fingerprint sensor and the biometric data comprises a fingerprint.

15. The system for verifying the identity of a patient of claim 10, wherein the patient biometric sensor comprises a capillary image capturing pulse oximeter and the biometric data comprises an image of capillaries.

* * * * *